US011879953B2

(12) United States Patent
Kuo et al.

(10) Patent No.: US 11,879,953 B2
(45) Date of Patent: Jan. 23, 2024

(54) SYSTEM AND METHOD TO EVALUATE UPPER GASTROINTESTINAL TRACT MOTILITY AND EMPTYING USING MAGNETIC RESONANCE IMAGING (MRI)

(71) Applicant: The General Hospital Corporation, Boston, MA (US)

(72) Inventors: Braden Kuo, Newton, MA (US); Christopher Nguyen, Cambridge, MA (US); Roberta Sclocco, Cambridge, MA (US); Vitaly Napadow, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/609,667

(22) PCT Filed: May 11, 2020

(86) PCT No.: PCT/US2020/032377
§ 371 (c)(1),
(2) Date: Nov. 8, 2021

(87) PCT Pub. No.: WO2020/227715
PCT Pub. Date: Nov. 12, 2020

(65) Prior Publication Data
US 2022/0214413 A1    Jul. 7, 2022

Related U.S. Application Data (60) Provisional application No. 62/845,456, filed on May 9, 2019.

(51) Int. Cl.
*G01R 33/48*    (2006.01)
*A61B 5/00*    (2006.01)
(Continued)

(52) U.S. Cl.
CPC ........ *G01R 33/4822* (2013.01); *A61B 5/0013* (2013.01); *A61B 5/055* (2013.01);
(Continued)

(58) Field of Classification Search
None
See application file for complete search history.

(56) References Cited

U.S. PATENT DOCUMENTS

2004/0054278 A1    3/2004    Kimchy et al.
2005/0074405 A1*    4/2005    Williams, III ..... A61K 49/0404
424/9.4

(Continued)

OTHER PUBLICATIONS

PCT/US2020/032377—International Search Report and Written Opinion—dated Aug. 10, 2020.
(Continued)

*Primary Examiner* — Rodney E Fuller
(74) *Attorney, Agent, or Firm* — Quarles & Brady LLP (57) ABSTRACT A method for evaluating gastric and upper small intestine motility and emptying in a gastrointestinal tract of a subject using magnetic resonance imaging includes administering a contrast agent to the subject; acquiring, using an MRI system, a set of MR data from the subject using a three-dimensional volumetric pulse sequence. The volumetric pulse sequence has a temporal resolution and a spatial resolution configured to facilitate measurement of volumetric and motility parameters. The method further includes reconstructing a set of images using the set of MR data, segmenting each image in the set of images to isolate a region of interest in the gastrointestinal tract of the subject, determining at least one volumetric and motility parameter based on the set of segmented images, and generating a report indicating the at least one volumetric or motility parameter.

22 Claims, 3 Drawing Sheets (51) Int. Cl.
    *A61B 5/055*    (2006.01)
    *G01R 33/56*   (2006.01)
(52) U.S. Cl.
    CPC .......... *A61B 5/4238* (2013.01); *A61B 5/7285* (2013.01); *G01R 33/5601* (2013.01); *G01R 33/5608* (2013.01); *A61B 2576/02* (2013.01)

(56) References Cited

U.S. PATENT DOCUMENTS

| | | |
|---|---|---|
| 2008/0260646 A1 | 10/2008 | Keller et al. |
| 2010/0106207 A1 | 4/2010 | Dobak |
| 2011/0044524 A1 | 2/2011 | Wang et al. |
| 2013/0216482 A1* | 8/2013 | Kwon .................. A61B 5/0071 424/9.6 |

OTHER PUBLICATIONS

Khalaf, et al., "Magnetic Resonance imaging Biomarkers of Gastrointestinal Motor Function and Fluid Distribution," World J Gastrointest Pathophysiology 2015; 6(4): 140-149.

Ha, et al., "Hemodynamic Measurement Using Four-Dimensional Phase-Contrast MRI: Quantification of Hemodynamic Parameters and Clinical Applications," pISSN 1229-6929—eISSN 2005-8330, Korean J Radiol 2016; 17 (4):445-462.

Gruber, et al., "RF Coils: a PRactical Guide for Nonphysicists," The Authors Journal of Magnetic Resonance Imaging, vol. 48, No. 3, 2018.

\* cited by examiner

SYSTEM AND METHOD TO EVALUATE UPPER GASTROINTESTINAL TRACT MOTILITY AND EMPTYING USING MAGNETIC RESONANCE IMAGING (MRI)

CROSS-REFERENCE TO RELATED APPLICATIONS

This application is a U.S. National Phase of International Application PCT/US2020/032377 filed May 11, 2020, which claims benefit of U.S. Provisional Patent Application 62/845,456, filed May 9, 2019. The contents of these applications are hereby incorporated by reference as set forth in their entirety herein.

STATEMENT REGARDING FEDERALLY SPONSORED RESEARCH OR DEVELOPMENT

This technology was made with government support under grants OT2-OD023867, R21DK116029 and R21EB024701, awarded by the National Institutes of Health. The government has certain rights in the technology.

FIELD

The present disclosure relates generally to magnetic resonance imaging (MRI) systems and methods and in particular, to a system and method for evaluating gastric motility and emptying using three- and four-dimensional MRI and providing volumetric measures in real time.

BACKGROUND

Gastric motility is the contraction of gastric muscle (peristalsis) to move food through the gastrointestinal tract (GI) tract and is controlled by a complex set of neural and hormonal signals. Gastric emptying is the natural process of emptying stomach contents into the duodenum. Evaluation and measurement of gastric motility and emptying may be used for the diagnosis of upper gut diseases such as functional dyspepsia and gastroparesis in an effort to explain patient symptom complaints with gastric and upper GI tract motility dysfunctions. Several technologies are currently used to measure and evaluate gastric motility and emptying including scintigraphy, two dimensional (2D) cine fluoroscopy, wireless motility capsule, SPECT scans and ultrasound. Typically, these techniques are only able to measure or evaluate a few of the various aspects of gastric motility and emptying such as total volume in and volume out. These techniques, however, do not provide volumetric measurements in real time granularity in terms of seconds and minutes. Scintigraphy also uses radioactive material as a contrast agent and is limited by the need to restrict exposure to ionizing radiation. Fluoroscopy uses barium and gastrogastrofin or other iodine-based contrast agents which have inherent contra-indications (e.g., children and pregnancy) and has x-ray dosage limits.

Therefore, there is a need for a system and method for evaluating gastric motility and emptying that provides different volumetric and 3D-resolved deformation measures in real time and does not require the use of ionizing radiation or radio-contrast agents. Volumetric measures in real time may allow assessment of the complex dynamics of contractility and volumes within the GI tract to investigate gastric accommodation and emptying.

SUMMARY

In accordance with an embodiment, a method for evaluating motility and emptying in a gastrointestinal tract of a subject using magnetic resonance imaging includes administering a contrast agent to the subject; acquiring, using an MRI system, a set of MR data from the subject using a three-dimensional volumetric pulse sequence having a temporal resolution and a spatial resolution configured to facilitate measurement of volumetric and motility parameters, reconstructing a set of images using the set of MR data, segmenting each image in the set of images to isolate a region of interest in the gastrointestinal tract of the subject, determining at least one volumetric or motility parameter based on the set of segmented images, and generating a report indicating the at least one volumetric or motility parameter.

In accordance with another embodiment, a magnetic resonance imaging (MRI) system includes a magnet system configured to generate a polarizing magnetic field about at least a portion of a subject, a magnetic gradient system including a plurality of gradient coils configured to apply at least one gradient field to the polarizing magnetic field, a radio frequency (RF) system configured to apply an excitation field to the subject and to receive MR data from the subject using coil array and a computer system. The computer system is programmed to acquire, after administration of a contrast agent, a set of MR data from the subject using a three-dimensional volumetric pulse sequence having a temporal resolution and a spatial resolution configured to facilitate measurement of volumetric and motility parameters, reconstruct a set of images using the set of MR data, segment each image in the set of images to isolate a region of interest in a gastrointestinal tract of the subject, determine at least one volumetric or motility parameter based on the set of segmented images, and generate a report indicating the at least one volumetric or motility parameter.

BRIEF DESCRIPTION OF THE DRAWINGS

The present disclosure will hereafter be described with reference to the accompanying drawings, wherein like reference numerals denote like elements.

DETAILED DESCRIPTION

Figure 1:
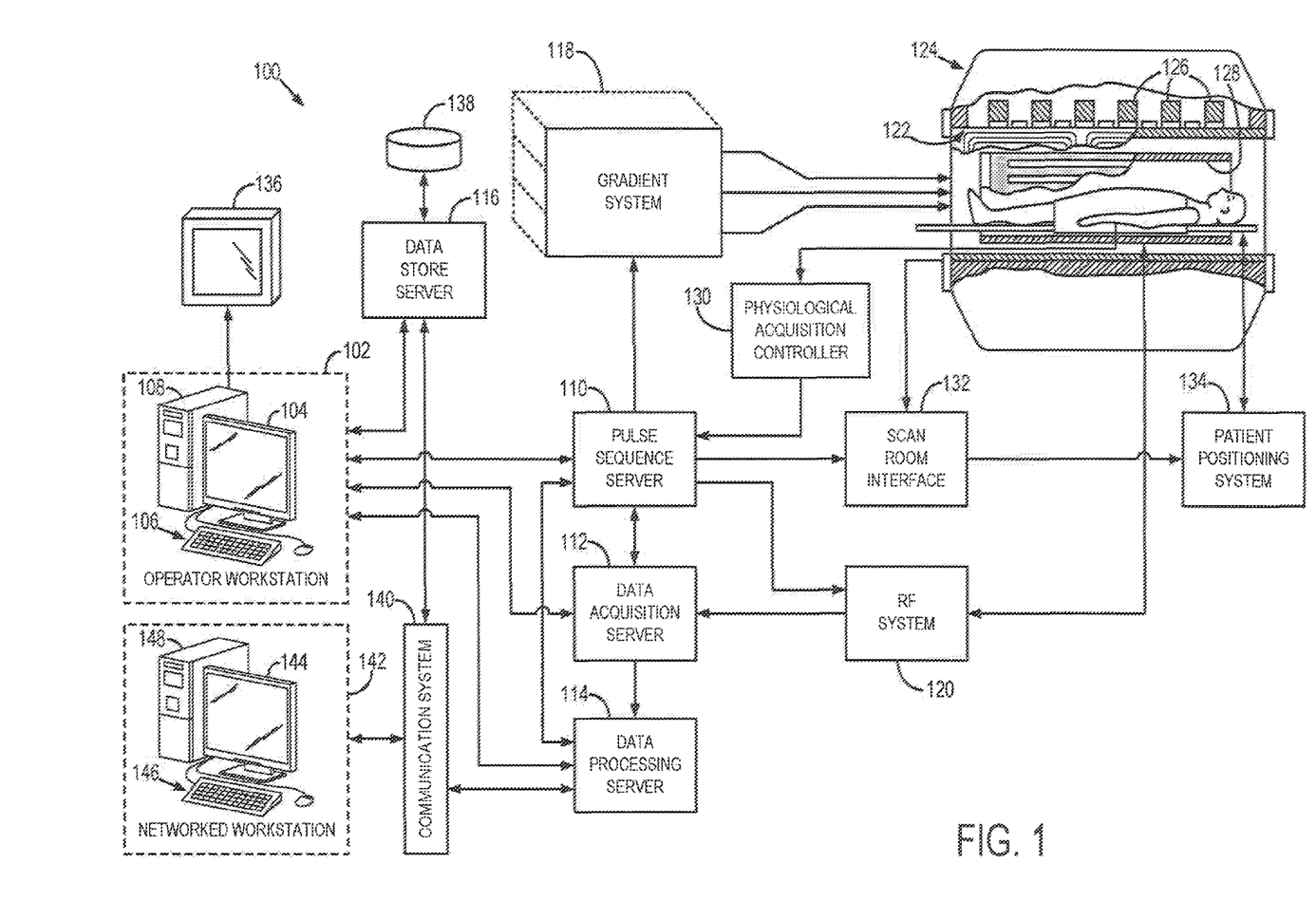
FIG. 1 is a block diagram of an example MRI system for use in accordance with an embodiment.

Referring now to FIG. 1, the disclosed systems and methods may be implemented using or designed to accompany a magnetic resonance imaging ("MRI") system 100, such as is illustrated in FIG. 1. The MRI system 100 includes an operator workstation 102, which will typically include a display 104, one or more input devices 106 (such as a keyboard and mouse or the like), and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to multiple servers, including a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms to perform the prescribed scan are produced and applied to the gradient system 118, which excites gradient coils in an assembly 122 to produce the magnetic field gradients $G_x$, $G_y$, $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \qquad \text{Eqn. 1;}$$

and the phase of the received magnetic resonance signal may also be determined according to the following relationship:

$$\varphi = \tan^{-1}\left(\frac{Q}{I}\right). \qquad \text{Eqn. 2}$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography ("MRA") scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction techniques, such as iterative or back-projection reconstruction techniques; applying filters to raw k-space data or to reconstructed images; generating functional magnetic resonance images; calculating motion or flow images; and so on.

Images reconstructed by the data processing server 114 are conveyed back to the operator workstation 102. Images may be output to operator display 112 or a display 136 that is located near the magnet assembly 124 for use by attending clinician. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144, one or more input devices 146 (such as a keyboard and mouse or the like), and a processor 148. The networked workstation 142 may be located within the same facility as the operator workstation 102, or in a different facility, such as a different healthcare institution or clinic. The networked workstation 142 may include a mobile device, including phones or tablets.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may exchange between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

The present disclosure describes a system and method for evaluating gastric motility and emptying for a region of interest in the gastrointestinal (GI) tract of a subject using magnetic imaging (MRI). Four-dimensional (4D) (i.e., 3D plus time) cine imaging is used to provide volumetric measures in real time which may be used to characterize gastric functions. Volumetric and motility measures (or parameters or indicies) are extracted from acquired 3D (or 4D) magnetic resonance (MR) data. The method may be used to quantify 3D or 4D gastric volume and motility metrics such as meal/air content separation, gastric emptying, gastric motility and pylorus dynamics. Dynamic 3D MRI data may be acquired from a region of the GI tract (e.g., the stomach) and analyzed to determine various indices (or parameters) including, for example, changes in contractility and volume over time. In addition, the method may be used to assess contrast meal and air content. These indices may be used to characterize and further define, for example, gastroparesis and functional dyspepsia, by highlighting specific and global upper GI motility dysfunction, and to assess the impact of therapeutic interventions. The disclosed MRI method utilizes a food-based contrast agent that does not include gadolinium or other iron-based contrast agents. By using a contrast agent without gadolinium or radiation, the system and method are more favorable for use with vulnerable populations such as, for example, pediatrics and pregnancy. In addition, MRI does not utilize ionizing radiation. The gastric 4D cine MRI technique is non-invasive and is capable of capturing complex dynamics of motility. The MRI technique provides 4D image data with excellent soft tissue contrast and without the risks of MRI contrast agents such as gadolinium.

Figure 2:
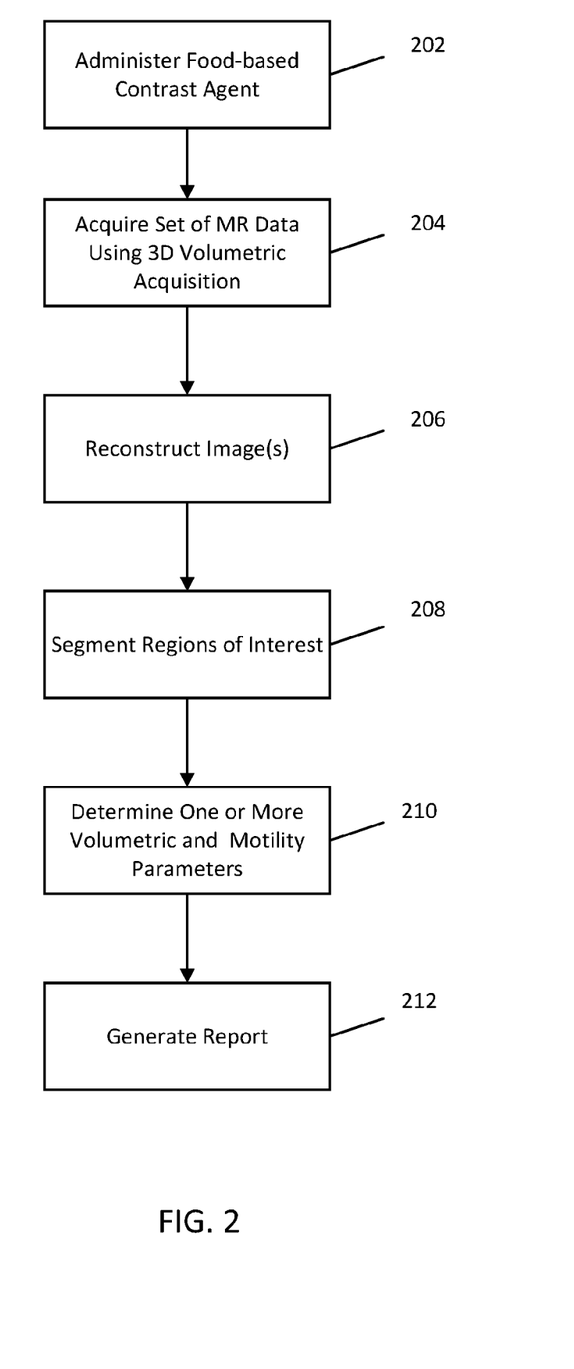
FIG. 2 illustrates a method for evaluating otility and emptying in a region of interest in a gastrointestinal tract in accordance with an embodiment.

FIG. 2 illustrates a method for evaluating motility and emptying in a region of interest in a gastrointestinal tract in accordance with an embodiment. At block 202, a food-based semi-solid contrast agent is administered to a subject (i.e., ingested by the subject). In an embodiment, the contrast meal is designed to be a paramagnetic contrast agent which shortens $T_1$ and $T_2$ contrast. The contrast agent (or meal) does not require gadolinium or other iron-based contrast agents. In an embodiment, the contrast agent is a pudding-based pineapple meal consisting of pudding infused with blended pineapple for high manganese content, thus providing excellent MRI contrast between, for example, stomach contents and non-stomach regions. In one example, a commercially available vanilla pudding may be infused with blended, fresh pineapple. At block 204, immediately following the ingestion of the contrast meal, MR data is acquired from a region of interest in the subject using, for example, an MRI system (e.g., MRI system 100 shown in FIG. 1). The region of interest may be a region (organ or other anatomy) in the gastrointestinal (GI) tract such as, for example, the stomach or small intestine, or may be a portion of the GI tract including more than one organ or other anatomy such as the upper GI tract or the lower GI tract. The MR data may be acquired using a real time 4D (i.e., 3D plus time) cine volumetric sequence. The pulse sequence may be, for example, a 3D stack of stars GRE FLASH sequence or other 3D volumetric sequence. The 3D or 4D volumetric sequence is configured to have a sufficient spatiotemporal resolution to facilitate measurement of volumetric gastric motility indices. In an embodiment, the temporal resolution is better than (i.e., less than or below) a first threshold and the spatial resolution is below a second threshold so that volumetric measures may be determined from the acquired MR data. In one example, the temporal resolution is better than (i.e., bless than or below) 10 s and the spatial resolution is less than 4 mm. In an embodiment, the pulse sequence does not require breath-holding (i.e., free-breathing). In an embodiment described further below with respect to FIG. 3, MR data may be acquired at a plurality of time points after the ingestion of the contrast meal to evaluate, for example, meal/air content separation and gastric emptying. The MR data may be stored in memory or data storage of, for example, an MRI system (e.g., the MRI system 100 of FIG. 1) or other computer system.

At block 206, a set of one or more 3D images is reconstructed from the MR data. The images may be reconstructed using known reconstruction methods. In an embodiment, motion correction may optionally be applied to the reconstructed images using known motion correction methods. The set of images may be stored in memory or data storage of, for example, an MRI system (e.g., the MRI system 100 of FIG. 1) or other computer system. At block 208, each image in the set of images is segmented to identify a region of interest in the GI tract. In one embodiment, the images are segmented to isolate an organ or other anatomy in the GI tract, for example, the stomach and to detect the boundaries of the organ or other anatomy, for example, the stomach on the images. In other embodiment, the images may be segmented to isolate the contrast meal and air content in the region of interest in the GI tract. The segmentation algorithm may be semi-automatic or automatic. At block 210, one or more volumetric or motility indices or metrics is determined (or extracted) based on the segmented set of images. For example, the indices (or measures or parameters) may include total volume (including contrast meal and air), contrast meal volume, air volume, rate of change of the total volume, rate of change of the contrast meal volume, rate of change of the air volume, the frequency of peristaltic waves, extent of lumen occlusion, uniformity of lumen occlusion, velocity of peristaltic waves, extent of wall deformation, deformation patterns, and wall strain and compliance. Known imaging processing methods may be used to extract the various volumetric and motility indices (or parameters). In an embodiment, gastric motility may be quantified with greater granularity across multiple parameters. The number of gastric voxels within each cross sectional plane of the acquired images provides time-varying cross-sectional area volumes at different locations along the gastric longitudinal axis. From these time series, parameters such as contraction, extent of lumen occlusion, and velocity of peristaltic waves propagation may be calculated. Additionally, 4D deformation fields may be generated by estimating the volume-to-volume spatial warping of the image. The 4D deformation fields may be used to evaluate spatial displacement of the gastric volume outer layer at any position. In another embodiment, pylorus dynamics may be quantified. Pylorus cross-sectional area may be assessed dynamically using the 4D MRI data and may be used to evaluate pyloric contraction parameters, such as luminal occlusion and frequency of contractions. Meal passing from the stomach through the pylorus may also be visualized exploiting MRI contrast. The determined (or extracted) indices (or parameters) may be used to, for example, characterize conditions such as gastroparesis and functional dyspepsia and may be used to assess therapeutic interventions. At block 212, a report may be generated indicating, for example, at least one of the determined volumetric or motility parameters, quantified metrics such as gastric motility and pylorus dynamics, etc., and one or more images from the set of images. The report may be provided to and shown on a display (e.g., display 104, 136 or 144 shown in FIG. 1). The segmented images and gastric volumetric and motility indices and metrics may be stored in memory or data storage of, for example, an MRI system (e.g., the MRI system 100 of FIG. 1) or other computer system.

Figure 3:
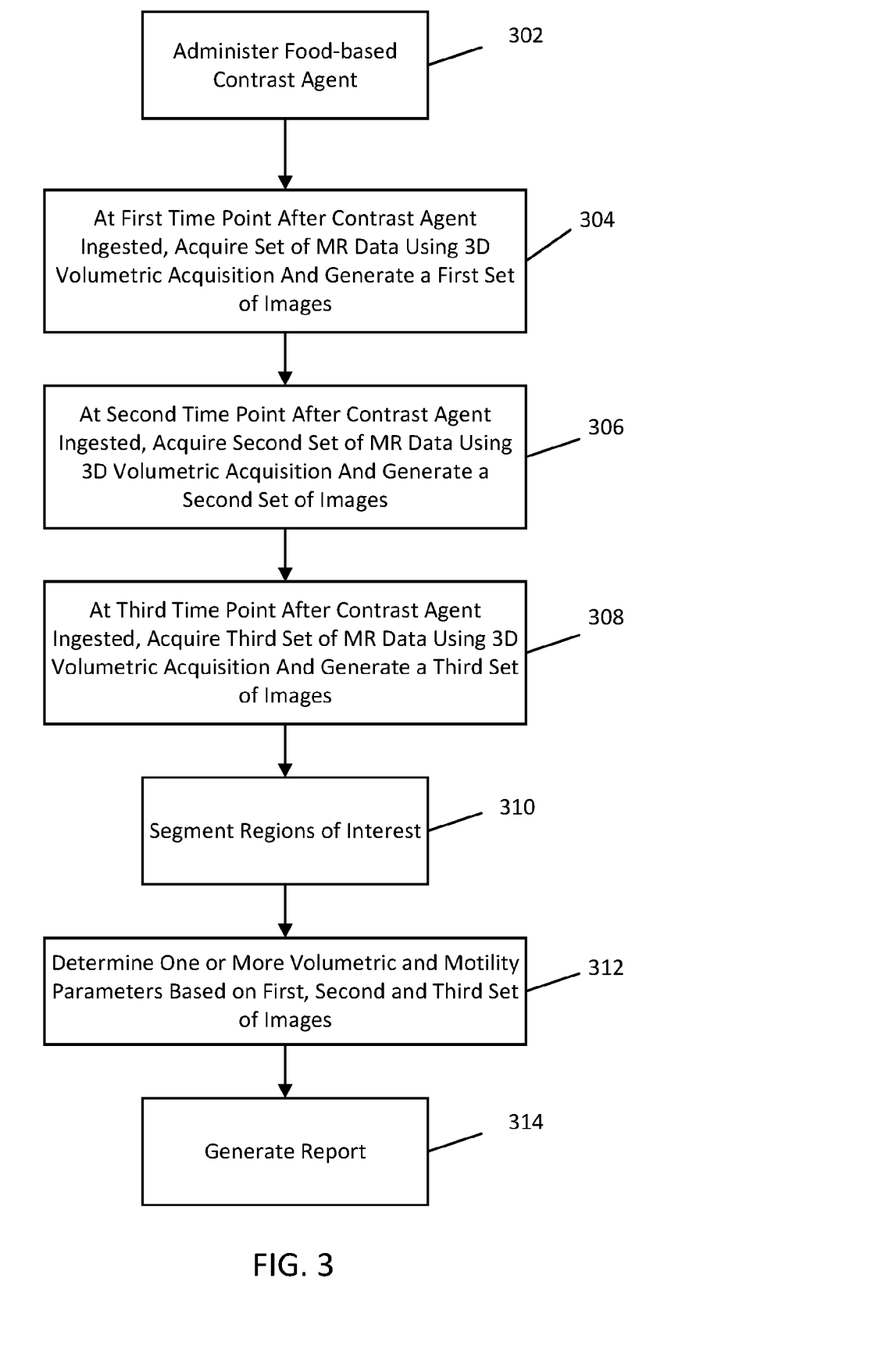
FIG. 3 illustrates a method for evaluating gastric motility and emptying in a region of interest in a gastrointestinal tract using a plurality of time points in accordance with an embodiment.

As mentioned above, in an embodiment 4D MR data may be acquired using the method described above with respect to FIG. 2 at a plurality of time points after the ingestion of the contrast meal to evaluate, for example, meal/air content separation and gastric emptying. FIG. 3 illustrates a method for evaluating motility and emptying in a region of interest in a gastrointestinal tract using a plurality of time points in accordance with an embodiment. In the embodiment shown in FIG. 2, MR data is acquired at a first time point, a second time point and a third time point after the ingestion of the contrast meal by the subject. For example, an MRI scan to acquire the MR data may be performed at 0, 20 and 40 minutes post contrast meal (T0, T1, T2, respectively), or at later times following meal ingestion, across the full time line for gastric emptying. In fact, while the following discussion refers to three time points post contrast meal, it should be understood that different numbers of time points may be used. At block 302, a food-based semi-solid contrast agent is administered to a subject (i.e., ingested by the subject). In an embodiment, the contrast meal is designed be a paramagnetic contrast agent which shortens $T_1$ and $T_2$ contrast. The contrast agent (or meal) does not require gadolinium or other iron-based contrast agents. In an embodiment, the contrast agents is a pudding based pineapple meal consisting of a pudding infused with blended pineapple for high manganese content. At block 304, immediately following the ingestion of the contrast meal a first set of MR data is acquired at a first time point (e.g., 0 minutes) from a region of interest in the subject using, for example, an MRI system (e.g., MRI system 100 shown in FIG. 1). The region of interest may be a region (organ or other anatomy) in the gastrointestinal (GI) tract such as, for example, the stomach or small intestine, or may be a portion of the GI tract including more than one organ or other anatomy such as the upper GI tract or the lower GI tract. As discussed above with respect to FIG. 2, the MR data may be acquired using a real time 4D (i.e., 3D plus time) cine volumetric sequence with a sufficient spatiotemporal resolution to facilitate measurement of volumetric gastric motility indices. A first set of images is reconstructed from the first set of MR data. At block 306, a second set of MR data is acquired at a second time point (e.g., 20 minutes) from the region of interest in the subject. A second set of images is reconstructed from the second set of MR data. At block 308, a third set of MR data is acquired at a third time point (e.g., 40 minutes) from the region of interest in the subject. A third set of images is reconstructed from the second set of MR data. The first, second and third set of MR data and the first, second and third set of images may be stored in memory or data storage of, for example, an MRI system (e.g., the MRI system 100 of FIG. 1) or other computer system.

At block 310, images in the first, second and third set of images are segmented to identify a region of interest in the GI tract. For example, one or more volumes in each MRI scan at each time point may be segmented to isolate the desired region of interest. In one embodiment, the images are segmented to isolate an organ or other anatomy in the GI tract, for example, the stomach and to detect the boundaries of the organ or other anatomy, for example, the stomach on the images. In other embodiment, the images may be segmented to isolate the contrast meal and air content in the region of interest in the GI tract. The segmentation algorithm may be semi-automatic or automatic. At block 312, one or more volumetric and motility indices or metrics is determined (or extracted) based on the segmented set of images. For example, the indices (or measures or parameters) may include total volume (including contrast meal and air), contrast meal volume, air volume, change in volume between time points for the total volume, contrast meal volume and air volume, rate of change of the total volume, rate of change of the contrast meal volume, rate of change of the air volume, the frequency of peristaltic waves, extent of lumen occlusion, uniformity of lumen occlusion, velocity of peristaltic waves, extent of wall deformation, deformation patterns, and wall strain and compliance. Known imaging processing methods may be used to extract the various volumetric and motility indices (or parameters). In an embodiment, meal/air content separation may be quantified. Following gastric segmentation, resulting volumes may be automatically separated into air and meal contents. Based on different MRI contrasts given by air and meal, an adaptive histogram-based thresholding procedure is applied to each gastric volume and time point, in order to separately evaluate meal and air contents over time. In another embodiment, gastric emptying may be quantified. Gastric volumes may be evaluated at each of the post-meal time points, as absolute values or as percent changes from the initial value, and for the entire region of interest, as well as for meal and air contents separately. The availability of volumetric time series allows the estimation of additional parameters, such as the speed of meal emptying.

At block 314, a report may be generated indicating, for example, at least one of the determined volumetric or motility parameters (or measures or indices), quantified metrics such as gastric motility and pylorus dynamics, meal/air content separation and gastric emptying, etc., and one or more images from the sets of images. The report may be provided to and shown on a display (e.g., display 104, 136 or 144 shown in FIG. 1). The segmented images and gastric volumetric and motility indices and metrics may be stored in memory or data storage of, for example, an MRI system (e.g., the MRI system 100 of FIG. 1) or other computer system.

The following example sets forth, in detail, ways in which the present disclosure was evaluated and ways in which the present disclosure may be used or implemented, and will enable one of ordinary skill in the art to more readily understand the principles thereof. The following examples are presented by way of illustration and are not meant to be limiting in any way.

In an example, the method was evaluated using healthy subjects who fasted overnight. Imaging of the stomach was performed immediately following ingestion of a food-based (gadolinium-free) MR contrast test meal by the subject. In this example, the contrast meal consisted of 400 ml of a lactose-free, high caloric (1140 kcl/400 ml) commercially available vanilla pudding infused with blended, fresh pineapple (for high manganese content). The MRI scan to acquire MR data was performed at 3T using a real-time 3D cine sequence not requiring breath holding at three time points, T0, T1, and T2, at 0, 20, and 40 minutes post-ingestion of the contrast meal, respectively. In this example the sequence was a 3D stack of stars GRE FLASH sequence with the following parameters: TR=2.7 ms, TE=1.14, FA=3 deg, temporal resolution=7 s, 40 slices, FOV=175 mm, 2.7 mm isotropic resolution), The first volume of each abdominal scan was segmented to isolate the stomach, and the total volume was calculated for each subject's post-meal time point. The dynamic 3D MRI allowed measure of stomach motility (frequency of peristaltic waves) within each 5-minute scan run. Semi-automated segmentation was implemented on all volumes and time points for a representative subject, and time-varying volumes were estimated for the whole stomach and separately for the fundus/corpus (proximal stomach) and antrum (distal stomach), as defined by mid-points of the lesser and greater curvatures.

In this example, volumetric measures showed a reduction in stomach volume from T0 to T2 (T0:527±78 ml; T1: 471±49 ml; 407±103 ml), as well as a slight increase in the frequency of peristaltic waves at T1 and T2 (T0: 2.0±0.3 cpm; T1: 3.2±0.5 cpm; T2: 3.2±0.2 cpm). Volumetric results from dynamic analysis showed a different behavior for the upper and lower parts of the stomach with the displacement of volume as expected from the proximal to distal stomach, and faster dynamics in distal stomach volumetric oscillations. The results of this example illustrate use of 3D dynamic volumetric MRI of the stomach to determine changes in contractility and volume changes with a meal over time. These measures can be applied to characterizations of gastroparesis and functional dyspepsia and the assessments of therapeutic interventions.

Computer-executable instructions for evaluating motility and emptying in a region of interest in a gastrointestinal tract in a subject according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access The present invention has been described in terms of one or more preferred embodiments, and it should be appreciated that many equivalents, alternatives, variations, and modifications, aside from those expressly stated, are possible and within the scope of the invention.

The invention claimed is:

1. A method for evaluating motility and emptying in a gastrointestinal tract of a subject using magnetic resonance imaging comprising:
administering a contrast agent to the subject;
acquiring, using an MRI system, a set of MR data from the subject using a three-dimensional volumetric pulse sequence having a temporal resolution and a spatial resolution configured to facilitate measurement of volumetric and motility parameters, wherein acquiring a set of MR data from the subject using a three-dimensional volumetric pulse sequence comprises:
acquiring a first set of MR data from the subject using the three-dimensional volumetric pulse sequence at a first time point after administration of the contrast agent;
acquiring a second set of MR data from the subject using the three-dimensional volumetric pulse sequence at a second time point after administration of the contrast agent; and
acquiring a third set of MR data from the subject using the three-dimensional volumetric pulse sequence at a third time point after administration of the contrast agent;
reconstructing a set of images using the set of MR data;
segmenting each image in the set of images to isolate a region of interest in the gastrointestinal tract of the subject;
determining at least one volumetric or motility parameter based on the set of segmented images; and
generating a report indicating the at least one volumetric or motility parameter.

2. The method according to claim 1, wherein the contrast agent is a food-based contrast agent.

3. The method according to claim 1, wherein the volumetric pulse sequence is configured to acquire four-dimensional MR data.

4. The method according to claim 1, wherein the temporal resolution is better than a first threshold and the spatial resolution is less than a second threshold.

5. The method according to claim 4, wherein the temporal resolution is better than 10 s and the spatial resolution is less than 4 mm.

6. The method according to claim 1, wherein the volumetric pulse sequence has a repetition time between three and seven seconds.

7. The method according to claim 1, wherein the region of interest in the gastrointestinal tract is a stomach.

8. The method according to claim 1, further comprising determining gastric motility based on the at least one volumetric or motility parameter.

9. The method according to claim 1, further comprising determining content separation of the contrast agent and air based on the at least one volumetric or motility parameter.

10. The method according to claim 1, further comprising determining gastric emptying based on the at least one volumetric or motility parameter.

11. The method according to claim 1, further comprising determining pylorus dynamics based on the at least one volumetric or motility parameter.

12. A magnetic resonance imaging (MRI) system comprising:
a magnet system configured to generate a polarizing magnetic field about at least a portion of a subject;
a magnetic gradient system including a plurality of gradient coils configured to apply at least one gradient field to the polarizing magnetic field;
a radio frequency (RF) system configured to apply an excitation field to the subject and to receive MR data from the subject using a coil array; and
a computer system programmed to:
acquire, after administration of a contrast agent, a set of MR data from the subject using a three-dimensional volumetric pulse sequence having a temporal resolution and a spatial resolution configured to facilitate measurement of volumetric and motility parameters, wherein acquiring a set of MR data from the subject using a three-dimensional volumetric pulse sequence comprises:
  acquiring a first set of MR data from the subject using the three-dimensional volumetric pulse sequence at a first time point after administration of the contrast agent;
  acquiring a second set of MR data from the subject using the three-dimensional volumetric pulse sequence at a second time point after administration of the contrast agent; and
  acquiring a third set of MR data from the subject using the three-dimensional volumetric pulse sequence at a third time point after administration of the contrast agent;
reconstruct a set of images using the set of MR data;
segment each image in the set of images to isolate a region of interest in a gastrointestinal tract of the subject;
determine at least one volumetric or motility parameter based on the set of segmented images; and
generate a report indicating the at least one volumetric or motility parameter.

13. The MRI system according to claim 12, wherein the contrast agent is a food-based contrast agent.

14. The MRI system according to claim 12, wherein the volumetric pulse sequence is configured to acquire four-dimensional MR data.

15. The MRI system according to claim 12, wherein the temporal resolution is better than a first threshold and the spatial resolution is less than a second threshold.

16. The MRI system according to claim 15, wherein the temporal resolution is better than 10 s and the spatial resolution is less than 4 mm.

17. The MRI system according to claim 12, wherein the volumetric pulse sequence has a repetition time between three and seven seconds.

18. The MRI system according to claim 12, wherein the region if interest in the gastrointestinal tract is a stomach.

19. The MRI system according to claim 12, further comprising determining gastric motility based on the at least one volumetric or motility parameter.

20. The MRI system according to claim 12, further comprising determining content separation of the contrast agent and air based on the at least one volumetric or motility parameter.

21. The MRI system according to claim 12, further comprising determining gastric emptying based on the at least one volumetric or motility parameter.

22. The MRI system according to claim 12, further comprising determining pylorus dynamics based on the at least one volumetric or motility parameter.

* * * * *

UNITED STATES PATENT AND TRADEMARK OFFICE
CERTIFICATE OF CORRECTION

PATENT NO. : 11,879,953 B2
APPLICATION NO. : 17/609667
DATED : January 23, 2024
INVENTOR(S) : Braden Kuo et al.

It is certified that error appears in the above-identified patent and that said Letters Patent is hereby corrected as shown below:

In the Specification

Column 5, Line 16, "magnetic imaging" should be --magnetic resonance imaging--.

Signed and Sealed this
Sixteenth Day of April, 2024

Katherine Kelly Vidal
*Director of the United States Patent and Trademark Office*